US00PP28300P3

(12) United States Plant Patent
Dragt

(10) Patent No.: US PP28,300 P3
(45) Date of Patent: Aug. 15, 2017

(54) ***HEUCHERELLA* PLANT NAMED 'INFINITY'**

(50) Latin Name: ×*Heucherella*
Varietal Denomination: Infinity

(71) Applicant: Joke Dragt, Zuidwolde (NL)

(72) Inventor: Joke Dragt, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 67 days.

(21) Appl. No.: 14/545,811

(22) Filed: Jun. 23, 2015

(65) Prior Publication Data

US 2016/0381856 P1 Dec. 29, 2016

(51) Int. Cl.
*A01H 5/12* (2006.01)

(52) U.S. Cl.
USPC ..... Plt./441

(58) Field of Classification Search
USPC ..... Plt./441, 440, 486
See application file for complete search history.

(56) References Cited

U.S. PATENT DOCUMENTS

PP21,859 P2 * 4/2011 Egger ..... Plt./440
PP25,723 P3 * 7/2015 Egger ..... Plt./441

OTHER PUBLICATIONS

New Plants and Flowers *Heucherella* pleasing most discerning gardener Jul. 9, 2014, retrieved on Oct. 17, 2016, retrieved from the Internet at <http://www.newplantsandflowers.com/heucherella-pleasing-most-discerning-gardener> 2 pp.*

Angela Treadwell—Palmer Plants Nouveau Do You Cultivate Jul. 4, 2014, retrieved on Oct. 17, 2016, retrieved from the Internet at <http://plantsnouveau.com/2014/07/04/do-you-cultivate_rest/> 5 pp.*

* cited by examiner

*Primary Examiner* — June Hwu
(74) *Attorney, Agent, or Firm* — C. A. Whealy

(57) ABSTRACT

A new and distinct cultivar of *Heucherella* plant named 'Infinity', characterized by its upright and uniformly mounded plant habit; moderately vigorous growth habit; silver and brown-colored leaves; dark to medium pink-colored flower buds; numerous sterile light pink to white-colored flowers held above the foliar plane on brown-colored peduncles; long flowering period; and excellent winter hardiness.

3 Drawing Sheets

Botanical designation: ×*Heucherella*.
Cultivar denomination: 'INFINITY'.

BACKGROUND OF THE INVENTION

The present invention relates to a new and distinct *Heucherella* plant, botanically known as ×*Heucherella* and hereinafter referred to by the name 'Infinity'.

The new *Heucherella* is a product of a planned breeding program conducted by the Inventor in Zuidwolde, The Netherlands. The objective of the breeding program is to create new long-flowering *Heucherella* plants that are winter hardy.

The new *Heucherella* plant originated from a cross-pollination conducted by the Inventor in Zuidwolde, The Netherlands in 2012 of *Heuchera* hybrid 'Shanghai', disclosed in U.S. Plant Pat. No. 21,859, as the female, or seed, parent with *Tiarella* hybrid 'Jeepers Creepers', disclosed in U.S. Plant Pat. No. 13,437 as the male, or pollen, parent. The new *Heucherella* plant was discovered and selected by the Inventor as a single flowering plant within the progeny of the stated cross-pollination in a controlled greenhouse environment in Zuidwolde, The Netherlands in 2013.

Asexual reproduction of the new *Heucherella* plant by stem cuttings in a controlled greenhouse environment in Zuidwolde, The Netherlands since 2013 has shown that the unique features of this new *Heucherella* plant are stable and reproduced true to type in successive generations.

SUMMARY OF THE INVENTION

The new *Heucherella* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Infinity'. These characteristics in combination distinguish 'Infinity' as anew and distinct *Heucherella* plant:

1. Upright and uniformly mounded plant habit.
2. Moderately vigorous growth habit.
3. Silver and brown-colored leaves.
4. Dark to medium pink-colored flower buds.
5. Numerous sterile light pink to white-colored flowers held above the foliar plane on brown-colored peduncles.
6. Long flowering period.
7. Excellent winter hardiness.

Plants of the new *Heucherella* differ from plants of the female parent, 'Shanghai', in length of flowering period as plants of the new *Heucherella* begin flowering earlier in the spring and flower later into the autumn than plants of 'Shanghai'. In addition, flowers of plants of the new *Heucherella* are sterile whereas flowers of plants of 'Shanghai' are fertile.

Plants of the new *Heucherella* differ from plants of the male parent, 'Jeepers Creepers', in length of flowering period as plants of the new *Heucherella* begin flowering early in the spring and flower late into the autumn whereas plants of 'Jeepers Creepers' only flower during the spring. Plants of the new *Heucherella* and 'Jeepers Creepers' differ in leaf color as plants of 'Jeepers Creepers' have green-colored leaves with red-colored venation. In addition, flowers of plants of the new *Heucherella* are sterile whereas flowers of plants of 'Jeepers Creepers' are fertile.

Plants of the new *Heucherella* can be compared to plants of *Heucherella* 'Cracked Ice', disclosed in U.S. Plant Pat. No. 24,690. In side-by-side comparisons in Zuidwolde, The Netherlands, plants of the new *Heucherella* differ from plants of 'Cracked Ice' in length of flowering period as plants of the new *Heucherella* begin flowering early in the spring and flower late into the autumn whereas plants of 'Cracked Ice' only flower during the summer. In addition, plants of the new *Heucherella* and 'Cracked Ice' differ in leaf margin undulation as leaves of plants of the new *Heucherella* have flat margins whereas leaves of plants of 'Cracked Ice' have ruffled margins.

Plants of the new *Heucherella* can also be compared to plants of *Heucherella* 'Gunsmoke', disclosed in U.S. Plant Pat. No. 22,395. In side-by-side comparisons conducted in Zuidwolde, The Netherlands, plants of the new *Heucherella* differ from plants of 'Gunsmoke' in length of flowering period as plants of the new *Heucherella* begin flowering early in the spring and flower late into the autumn whereas plants of 'Gunsmoke' only flower during the summer. In addition, plants of the new *Heucherella* and 'Gunsmoke' differ in leaf color as leaves of plants of 'Gunsmoke' are red and silver in color.

BRIEF DESCRIPTION OF THE PHOTOGRAPHS

The accompanying colored photographs illustrate the overall appearance of the new *Heucherella* plant showing the colors as true as it is reasonably possible to obtain in colored reproductions of this type. Colors in the photographs may differ slightly from the color values cited in the detailed botanical description which accurately describe the colors of the new *Heucherella* plant.

The photograph on the first sheet is a side perspective view of a typical plant of 'Infinity' grown in a container.

The photograph on the second sheet is a close-up view of typical leaves of 'Infinity'.

The photograph on the third sheet is a close-up view of typical inflorescences of 'Infinity'.

DETAILED BOTANICAL DESCRIPTION

The aforementioned photograph and following observations, measurements and values describe plants grown during the summer in 23-cm containers in an outdoor nursery in Zuidwolde, The Netherlands and under cultural practices typical of commercial *Heucherella* production. During the production of the plants, day temperatures ranged from 15° C. to 32° C. and night temperatures ranged from 6° C. to 20° C. Plants were one year old when the photographs and the description were taken. In the following description, color references are made to The Royal Horticultural Society Colour Chart, 2007 Edition, except where general terms of ordinary dictionary significance are used.

Botanical classification: ×*Heucherella* 'Infinity'.

Parentage:

*Female, or seed, parent.*—*Heuchera* hybrid 'Shanghai', disclosed in U.S. Plant Pat. No. 21,859.

*Male, or pollen, parent.*—*Tiarella* hybrid 'Jeepers Creepers', disclosed in U.S. Plant Pat. No. 13,437.

Propagation:

*Type*.—By meristem culture.

*Time to initiate roots, summer*.—About two weeks at temperatures about 20° C.

*Time to produce a rooted young plant, summer*.—About two months at temperatures about 20° C.

*Root description*.—Medium in thickness, fibrous; creamy white in color.

*Rooting habit*.—Moderately freely branching; medium density.

Plant description:

*Plant and growth habit*.—Herbaceous perennial; basal rosette plant habit with leaves developing from the base; upright and uniformly mounded plant habit; moderately vigorous growth habit.

*Plant height, soil level to top of inflorescences*.—About 50.2 cm.

*Plant diameter or spread*.—About 55.3 cm.

Leaf description:

*Arrangement*.—Leaves arranged in basal rosettes, about 13 leaves developing per rosette; leaves simple.

*Length*.—About 10.4 cm.

*Width*.—About 9.3 cm.

*Shape*.—Palmately and moderate to deeply-lobed; not undulate.

*Apex*.—Rounded acute.

*Base*.—Hastate, not imbricate.

*Margin*.—Lobed; crenate with ciliation.

*Texture and luster, upper surface*.—Pubescent, velvety; matte.

*Texture and luster, lower surface*.—Pubescent, pubescence more prominent along veins; moderately glossy.

*Venation pattern*.—Palmate.

*Color*.—Developing leaves, upper surface: Close to 200B; towards the margins, close to N199B. Developing leaves, lower surface: Close to N186C; towards the margins, close to 200B. Fully expanded leaves, upper surface: Interveinal areas, close to between N200B and 201A and along the veins, close to lighter than between 200A and 203A; venation, close to 152A, proximally, close to 144A to 144B. Fully expanded leaves, lower surface: Lighter than between N186C and 200B; venation, close to 197B to 197C.

*Petioles*.—Length: About 13.2 cm. Diameter: About 2 mm. Texture, upper and lower surfaces: Pubescent. Color, upper and lower surfaces: Close to 197A; towards the base, strongly tinged with close to N186C.

Flower description:

*Flower type and flowering habit*.—Single campanulate flowers arranged on mostly upright axillary simple or compound spikes; each simple spike with about 38 flowers and each compound spike with about 110 flowers; about 2,500 flowers per plant develop over the flowering season; flowers face mostly outward to slightly upright.

*Fragrance*.—Faintly fragrant, sweet.

*Time of flowering*.—Long flowering period, plants begin flowering in April and continue flowering until October in The Netherlands.

*Flower longevity*.—Individual flowers last about five days on the plant; flowers not persistent.

*Inflorescence length* (*lowest flower to terminal flower*).—About 15.1 cm.

*Inflorescence width*.—Simple spikes, about 3.4 cm; compound spikes, about 10.1 cm.

*Flower diameter*.—About 8 mm.

*Flower depth* (*height*).—About 5 mm.

*Flower buds*.—Height: About 3 mm. Diameter: About 2 mm. Shape: Ovate. Color: Close to 62A; towards the base, close to 58D; less mature flower buds are darker in color, close to 58A to 58B.

*Petals*.—Quantity and arrangement: Five petals in a single whorl. Length: About 4 mm. Width: About 1 mm. Shape: Elliptic. Apex: Acute. Margin: Entire. Texture, upper and lower surfaces: Smooth, glabrous. Color: When opening, upper and lower surfaces: Close to N155B. Fully opened, upper and lower surfaces: Close to NN155C to NN155D.

*Sepals*.—Quantity and arrangement: Five sepals, fused. Length: About 4.5 mm. Width: About 2 mm; calyx diameter, about 7 mm. Shape: Roughly oblong. Apex: Obtuse. Margin: Entire, fused. Texture, upper and lower surfaces: Densely pubescent. Color: When opening, upper surface: Close to N155B. When opening, lower surface: Close to 62D; towards the base, close to 58D. Fully opened, upper surface: Close to N155B. Fully opened, lower surface: Between 62D and N155B.

*Peduncles*.—Length, primary peduncles: About 44.4 cm. Length, lateral peduncles: About 9.5 cm. Diameter, primary peduncles: About 2.5 mm. Diameter, lateral peduncles: About 1.5 mm. Strength: Moderately strong. Aspect, primary peduncles: About 20° from vertical. Aspect, lateral peduncles: About 40° from primary peduncle axis. Texture: Pubescent. Color: Close to N199A.

*Pedicels*.—Length: About 5 mm. Diameter: About 0.5 mm. Strength: Moderately strong. Aspect: About 35° from peduncle axis. Texture: Pubescent. Color: Close to 152C to 152D; color becoming closer to N199A with development.

*Reproductive organs*.—Androecium: Stamen number: Eight per flower. Filament length: About 3 mm. Filament color: Close to NN155C to NN155D. Anther length: About 0.35 mm. Anther shape: Oval. Anther color: Close to 164C. Amount of pollen: None observed. Gynoecium: Pistil number: Two per flower. Pistil length: About 2 mm. Stigma shape: Pointed. Stigma color: Close to 160D. Style length: About 1.8 mm. Style color: Close to 155A. Ovary color: Close to 155A.

*Seeds*.—Seed production has not been observed on plants of the new *Heucherella*; flowers are sterile.

Disease & pest resistance: Resistance to pathogens and pests has not been observed on plants of the new *Heucherella* grown under commercial conditions.

Winter hardiness: Plants of the new *Heucherella* have been observed to have excellent winter hardiness and to be suitable for USDA Hardiness Zone 3.

It is claimed:

1. A new and distinct *Heucherella* plant named 'Infinity' as illustrated and described.

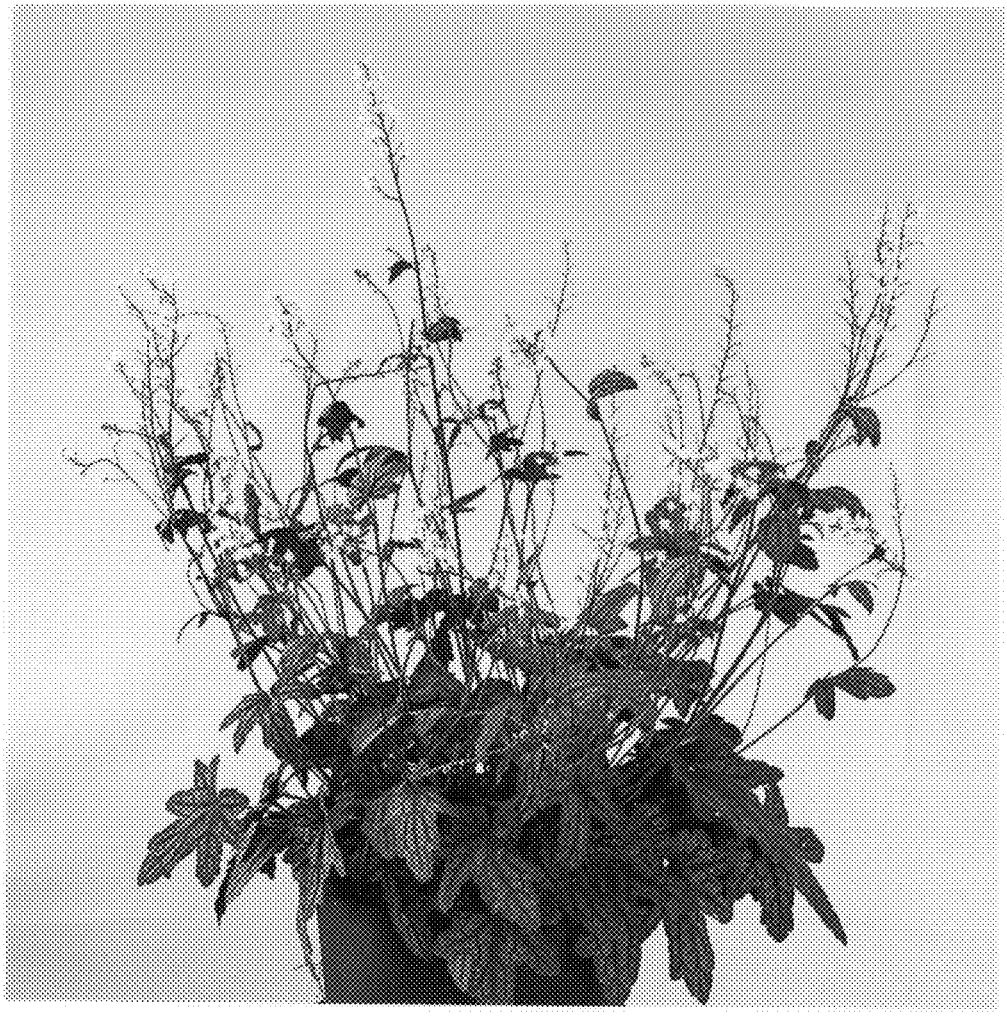

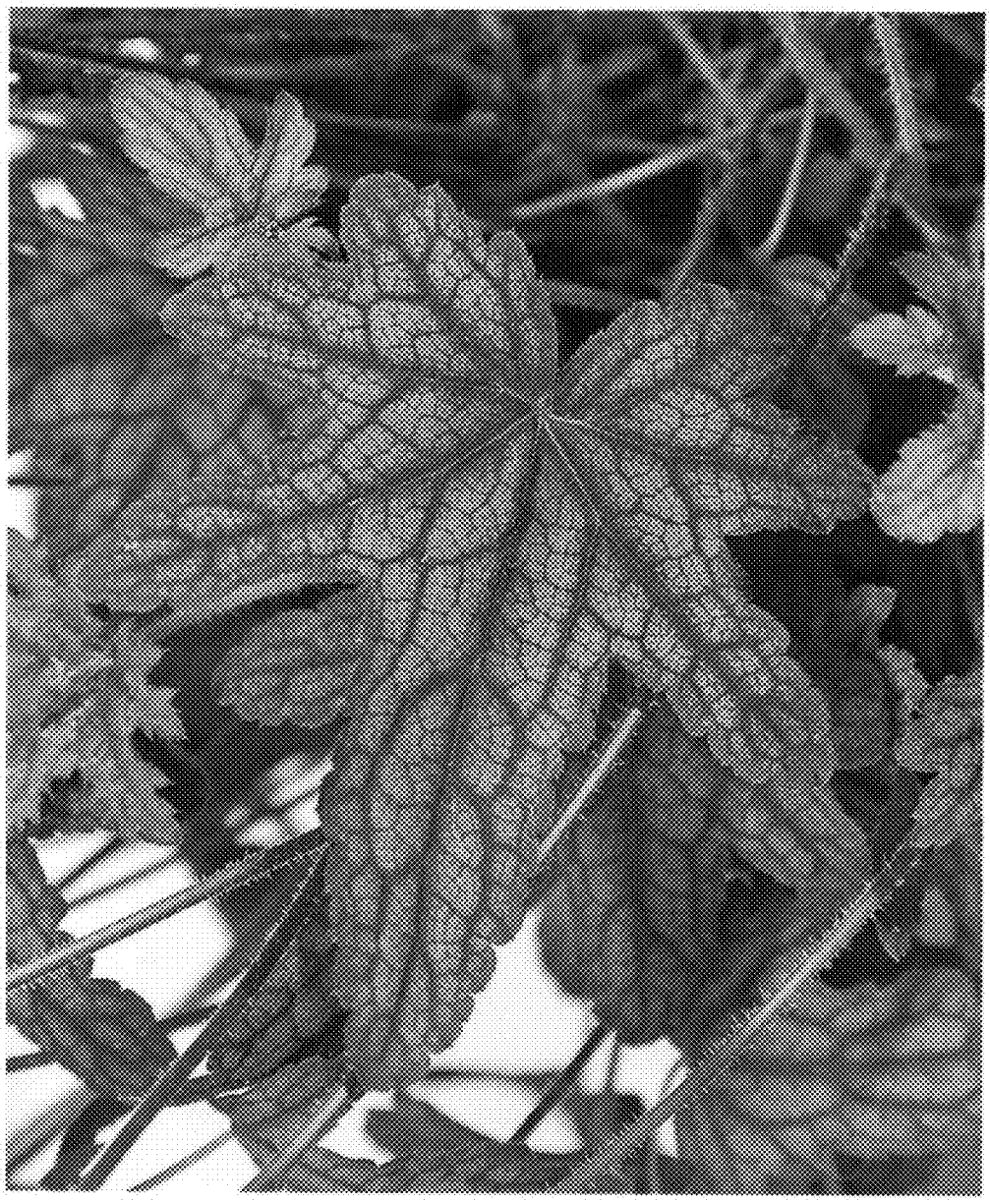

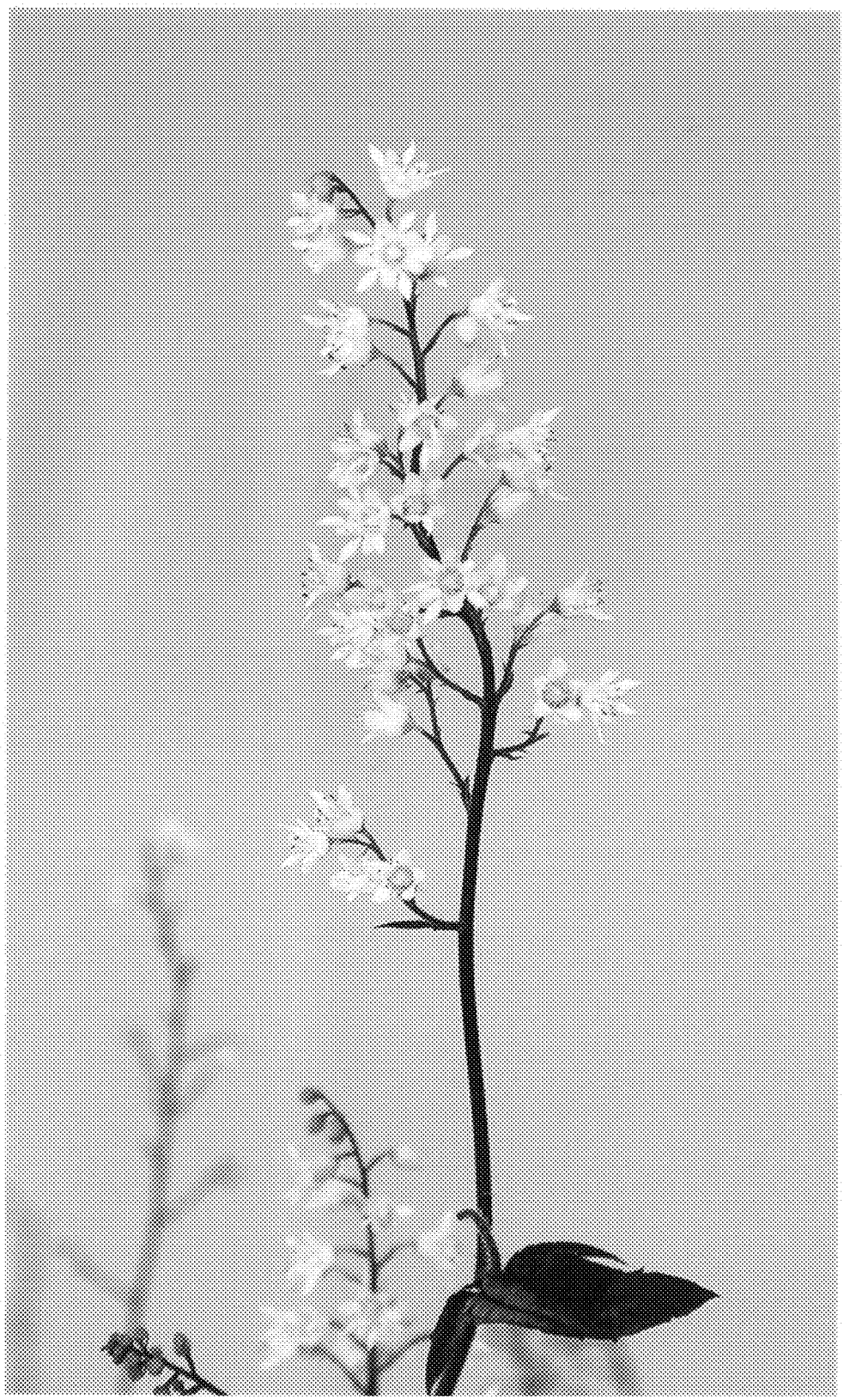

* * * * *